United States Patent
Gale et al.

(10) Patent No.: US 7,229,471 B2
(45) Date of Patent: Jun. 12, 2007

(54) COMPOSITIONS CONTAINING FAST-LEACHING PLASTICIZERS FOR IMPROVED PERFORMANCE OF MEDICAL DEVICES

(75) Inventors: David C. Gale, Sunnyvale, CA (US); Klaus Kleine, Los Gatos, CA (US); Anthony J. Abbate, Santa Clara, CA (US); Svava Maria Atladottir, San Francisco, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2 days.

(21) Appl. No.: 10/937,975

(22) Filed: Sep. 10, 2004

(65) Prior Publication Data

US 2006/0058868 A1    Mar. 16, 2006

(51) Int. Cl.
*A61F 2/06* (2006.01)
*A61M 29/00* (2006.01)

(52) U.S. Cl. .................... 623/1.15; 606/200

(58) Field of Classification Search .............. 623/1.15; 606/200
See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |

(Continued)

FOREIGN PATENT DOCUMENTS

DE    44 07 079    9/1994

(Continued)

OTHER PUBLICATIONS

U.S. Appl. No. 10/317,435, filed Dec. 11, 2002, Hossainy et al.

(Continued)

*Primary Examiner*—Corrine McDermott
*Assistant Examiner*—Thomas J Sweet
(74) *Attorney, Agent, or Firm*—Squire, Sanders & Dempsey L.L.P.

(57) ABSTRACT

Medical implants containing a temporary plasticizer, methods of producing such implants, and methods of using the implants in treating a disease, or ameliorating one or more symptoms thereof, in a subject are provided.

20 Claims, 4 Drawing Sheets

U.S. PATENT DOCUMENTS

| | | |
|---|---|---|
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury et al. |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar et al. |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |

| | | | | | | |
|---|---|---|---|---|---|---|
| 5,986,169 | A | 11/1999 | Gjunter | 6,485,512 | B1 | 11/2002 | Cheng |
| 5,997,468 | A | 12/1999 | Wolff et al. | 6,492,615 | B1 | 12/2002 | Flanagan |
| 6,010,445 | A | 1/2000 | Armini et al. | 6,494,908 | B1 | 12/2002 | Huxel et al. |
| 6,015,541 | A | 1/2000 | Greff et al. | 6,495,156 | B2 | 12/2002 | Wenz et al. |
| 6,042,875 | A | 3/2000 | Ding et al. | 6,511,748 | B1 | 1/2003 | Barrows |
| 6,048,964 | A | 4/2000 | Lee et al. | 6,517,888 | B1 | 2/2003 | Weber |
| 6,051,648 | A | 4/2000 | Rhee et al. | 6,527,801 | B1 | 3/2003 | Dutta |
| 6,056,993 | A | 5/2000 | Leidner et al. | 6,537,589 | B1 | 3/2003 | Chae et al. |
| 6,060,451 | A | 5/2000 | DiMaio et al. | 6,539,607 | B1 | 4/2003 | Fehring et al. |
| 6,066,156 | A | 5/2000 | Yan | 6,540,777 | B2 | 4/2003 | Stenzel |
| 6,071,266 | A | 6/2000 | Kelley | 6,554,854 | B1 | 4/2003 | Flanagan |
| 6,074,659 | A | 6/2000 | Kunz et al. | 6,565,599 | B1 | 5/2003 | Hong et al. |
| 6,080,177 | A | 6/2000 | Igaki et al. | 6,569,191 | B1 | 5/2003 | Hogan |
| 6,080,488 | A | 6/2000 | Hostettler et al. | 6,569,193 | B1 | 5/2003 | Cox et al. |
| 6,083,258 | A | 7/2000 | Yadav | 6,572,672 | B2 | 6/2003 | Yadav et al. |
| 6,093,463 | A | 7/2000 | Thakrar | 6,574,851 | B1 | 6/2003 | Mirizzi |
| 6,096,070 | A | 8/2000 | Ragheb et al. | 6,585,755 | B2 | 7/2003 | Jackson et al. |
| 6,096,525 | A | 8/2000 | Patnaik | 6,592,614 | B2 | 7/2003 | Lenker et al. |
| 6,099,562 | A | 8/2000 | Ding et al. | 6,592,617 | B2 | 7/2003 | Thompson |
| 6,103,230 | A | 8/2000 | Billiar et al. | 6,613,072 | B2 | 9/2003 | Lau et al. |
| 6,107,416 | A | 8/2000 | Patnaik et al. | 6,626,939 | B1 | 9/2003 | Burnside et al. |
| 6,110,188 | A | 8/2000 | Narciso, Jr. | 6,635,269 | B1 | 10/2003 | Jennissen |
| 6,110,483 | A | 8/2000 | Whitbourne et al. | 6,645,243 | B2 | 11/2003 | Vallana et al. |
| 6,113,629 | A | 9/2000 | Ken | 6,656,162 | B2 | 12/2003 | Santini, Jr. et al. |
| 6,117,979 | A | 9/2000 | Hendriks et al. | 6,664,335 | B2 | 12/2003 | Krishnan |
| 6,120,536 | A | 9/2000 | Ding et al. | 6,666,214 | B2 | 12/2003 | Canham |
| 6,120,904 | A | 9/2000 | Hostettler et al. | 6,667,049 | B2 | 12/2003 | Janas et al. |
| 6,121,027 | A | 9/2000 | Clapper et al. | 6,669,723 | B2 | 12/2003 | Killion et al. |
| 6,125,523 | A | 10/2000 | Brown et al. | 6,676,697 | B1 | 1/2004 | Richter |
| 6,127,173 | A | 10/2000 | Eckstein et al. | 6,679,980 | B1 | 1/2004 | Andreacchi |
| 6,129,761 | A | 10/2000 | Hubbell | 6,689,375 | B1 | 2/2004 | Wahlig et al. |
| 6,129,928 | A | 10/2000 | Sarangapani et al. | 6,695,920 | B1 | 2/2004 | Pacetti et al. |
| 6,150,630 | A | 11/2000 | Perry et al. | 6,706,273 | B1 | 3/2004 | Roessler |
| 6,153,252 | A | 11/2000 | Hossainy et al. | 6,709,379 | B1 | 3/2004 | Brandau et al. |
| 6,159,951 | A | 12/2000 | Karpeisky et al. | 6,719,934 | B2 | 4/2004 | Stinson |
| 6,160,084 | A | 12/2000 | Langer et al. | 6,719,989 | B1 | 4/2004 | Matsushima et al. |
| 6,165,212 | A | 12/2000 | Dereume et al. | 6,720,402 | B2 | 4/2004 | Langer et al. |
| 6,166,130 | A | 12/2000 | Rhee et al. | 6,746,773 | B2 | 6/2004 | Llanos et al. |
| 6,169,170 | B1 | 1/2001 | Gryaznov et al. | 6,752,826 | B2 | 6/2004 | Holloway et al. |
| 6,171,609 | B1 | 1/2001 | Kunz | 6,753,007 | B2 | 6/2004 | Haggard et al. |
| 6,174,330 | B1 | 1/2001 | Stinson | 6,764,505 | B1 | 7/2004 | Hossainy et al. |
| 6,177,523 | B1 | 1/2001 | Reich et al. | 6,818,063 | B1 | 11/2004 | Kerrigan |
| 6,183,505 | B1 | 2/2001 | Mohn, Jr. et al. | 6,846,323 | B2 | 1/2005 | Yip et al. |
| 6,187,045 | B1 | 2/2001 | Fehring et al. | 2001/0009769 | A1 | 7/2001 | Williams et al. |
| 6,210,715 | B1 | 4/2001 | Starling et al. | 2001/0044652 | A1 | 11/2001 | Moore |
| 6,224,626 | B1 | 5/2001 | Steinke | 2002/0002399 | A1 | 1/2002 | Huxel et al. |
| 6,228,845 | B1 | 5/2001 | Donovan et al. | 2002/0004060 | A1 | 1/2002 | Heublein et al. |
| 6,240,616 | B1 | 6/2001 | Yan | 2002/0004101 | A1 | 1/2002 | Ding et al. |
| 6,245,076 | B1 | 6/2001 | Yan | 2002/0062148 | A1 | 5/2002 | Hart |
| 6,245,103 | B1 | 6/2001 | Stinson | 2002/0065553 | A1 | 5/2002 | Weber |
| 6,248,344 | B1 | 6/2001 | Ylanen et al. | 2002/0111590 | A1 | 8/2002 | Davila et al. |
| 6,251,135 | B1 | 6/2001 | Stinson et al. | 2002/0116050 | A1 | 8/2002 | Kocur |
| 6,251,142 | B1 | 6/2001 | Bernacca et al. | 2002/0138133 | A1 | 9/2002 | Lenz et al. |
| 6,273,913 | B1 | 8/2001 | Wright et al. | 2002/0161114 | A1 | 10/2002 | Gunatillake et al. |
| 6,281,262 | B1 | 8/2001 | Shikinami | 2003/0033001 | A1 | 2/2003 | Igaki |
| 6,284,333 | B1 | 9/2001 | Wang et al. | 2003/0093107 | A1 | 5/2003 | Parsonage et al. |
| 6,287,332 | B1 | 9/2001 | Bolz et al. | 2003/0100865 | A1 | 5/2003 | Santini, Jr. et al. |
| 6,290,721 | B1 | 9/2001 | Heath | 2003/0105518 | A1 | 6/2003 | Dutta |
| 6,293,966 | B1 | 9/2001 | Frantzen | 2003/0105530 | A1 | 6/2003 | Pirhonen |
| 6,303,901 | B1 | 10/2001 | Perry et al. | 2003/0171053 | A1 | 9/2003 | Sanders |
| 6,312,459 | B1 | 11/2001 | Huang et al. | 2003/0187495 | A1 | 10/2003 | Cully et al. |
| 6,327,772 | B1 | 12/2001 | Zadno-Azizi et al. | 2003/0208259 | A1 | 11/2003 | Penhasi |
| 6,375,826 | B1 | 4/2002 | Wang et al. | 2003/0209835 | A1 | 11/2003 | Chun et al. |
| 6,379,381 | B1 | 4/2002 | Hossainy et al. | 2003/0226833 | A1 | 12/2003 | Shapovalov et al. |
| 6,387,121 | B1 | 5/2002 | Alt | 2003/0236320 | A1 | 12/2003 | Martin et al. |
| 6,388,043 | B1 | 5/2002 | Langer et al. | 2003/0236565 | A1 | 12/2003 | Fifer |
| 6,395,326 | B1 | 5/2002 | Castro et al. | 2004/0093077 | A1 | 5/2004 | White et al. |
| 6,409,761 | B1 | 6/2002 | Jang | 2004/0098095 | A1 | 5/2004 | Burnside et al. |
| 6,423,092 | B2 | 7/2002 | Datta et al. | 2004/0106987 | A1 | 6/2004 | Palasis et al. |
| 6,461,632 | B1 | 10/2002 | Gogolewski | 2004/0111149 | A1 | 6/2004 | Stinson |
| 6,464,720 | B2 | 10/2002 | Boatman et al. | 2004/0127970 | A1 | 7/2004 | Weber |
| 6,475,779 | B2 * | 11/2002 | Mathiowitz et al. ..... 435/320.1 | 2004/0143180 | A1 | 7/2004 | Zhong et al. |
| 6,479,565 | B1 | 11/2002 | Stanley | 2004/0143317 | A1 | 7/2004 | Stinson et al. |

| | | | |
|---|---|---|---|
| 2004/0167610 | A1 | 8/2004 | Fleming, III |
| 2005/0147647 | A1 | 7/2005 | Glauser et al. |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |
| WO | WO 2004/112863 | 12/2004 |

OTHER PUBLICATIONS

Anonymous, *Bioabsorbable stent mounted on a catheter having optical coherence tomography capabilities*, Research Disclosure, Sep. 2004, pp. 1159-1162.
Ansari, *Tubal Reanastomosis Using Absorbable Stent*, International Journal of Fertility, vol. 23, No. 4, pp. 242-243 (1978).
Ansari, *End-to-end tubal anastomosis using an absorbable stent*, Fertility and Sterility, vol. 32(2), pp. 197-201 (Aug. 1979).
Bull, *Parylene Coating for Medical Applications*, Medical Product Manufacturing News 1 pg. (Mar. 1993).
Casper et al., *Fiber-Reinforced Absorbable Composite for Orthopedic Surgery*, Polymeric Materials Science and Engineering, 53: pp. 497-501 (1985).
Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Devanathan et al., *Polymeric Conformal Coatings for Implantable Electronic Devices*, IEEE Transactions on Biomedical Engineering, vol. BME-27(11), pp. 671-675 (1980).
Elbert et al., *Conjugate Addition Reactions Combined with Free-Radical Cross-Linking for the Design of Materials for Tissue Engineering*, Biomacromolecules 2, pp. 430-441 (2001).
Feng-Chun et al., *Assessment of Tissue Blood Flow Following Small Artery Welding with an Intraluminal Dissolvable Stent*, Microsurgery, vol. 19(3), pp. 148-152 (1999).
Hahn et al., *Glow Discharge Polymers as Coatings for Implanted Devices*, ISA, pp. 109-111 (1981).
Hahn et al., *Biocompatibility of Glow-Discharge-Polymerized Films and Vacuum-Deposited Parylene*, J Applied Polymer Sci, 38, pp. 55-64 (1984).
Kelley et al., *Totally Resorbable High-Strength Composite Material*, Advances in Biomedical Polymers, 35, pp. 75-85 (1987).
Kubies et al., *Microdomain Structure In polylactide-block-poly(ethylene oxide) copolymer films*, Biomaterials 21, pp. 529-536 (2000).
Kutryk et al., *Coronary Stenting: Current Perspectives*, a companion to the Handbook of Coronary Stents 16 pgs. (1999).
Mauduit et al., *Hydrolytic degradation of films prepared from blends of high and low molecular weight poly(DL-lactic acid)s*, J. Biomed. Mater. Res. v. 30, pp. 201-207 (1996).
Martin et al., *Enhancing the biological activity of immobilized osteopontin using a type-1 collagen affinity coating*, J. Biomed. Mater Res 70A, pp. 10-19 (2004).
Middleton et al., *Synthetic biodegradable polymers as orthopedic devices*, Biomaterials, vol. 21, pp. 2335-2346 (2000).
Muller et al., *Advances in Coronary Angioplasty: Endovascular Stents*, Coron. Arter. Dis., 1(4), pp. 438-448 (Jul./Aug. 1990).
Nichols et al., *Electrical Insulation of Implantable Devices by Composite Polymer Coatings*, ISA Transactions, 26(4), pp. 15-18 (1987).
Peuster et al., *A novel approach to temporary stenting: degradable cardiovascular stents produced from corrodible metal-results 6-18 months after implantation into New Zealand white rabbits*, Heart 86, pp. 563-569 (2001).
Pietrzak et al., *Bioresorbable implants—practical considerations*, Bone v. 19, no. 1, Supplement Jul. 1996: 109S-119S.
Pietrzak et al., *Bioabsorbable Fixation Device: Status for the Craniomaxillofacial Surgeon*, J. Craniofaxial Surg. 2, pp. 92-96 (1997).
von Recum et al., *Degradation of polydispersed poly(L-lactic acid) to modulate lactic acid release*, Biomaterials 16, pp. 441-445 (1995).
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).
Schatz, *A View of Vascular Stents*, Circulation, 79(2), pp. 445-457 (Feb. 1989).
Schmidt et al., *Long-Term Implants of Parylene-C Coated Microelectrodes*, Med & Biol Eng & Comp, 26(1), pp. 96-101 (Jan. 1988).
Spagnuolo et al., *Gas 1 is induced by VE-cadherin and vascular endothelial growth factor and inhibits endothelial cell apoptosis*, Blood 103, pp. 3005-3012 (2004).
Tamai et al., *Initial and 6-Month Results of Biodegradable Poly-l-Lactic Acid Coronary Stents in Humans*, Circulation , pp. 399-404 (2000).
Tsui et al., *Biodegradable Polymeric Stents*, Current Interventional Cardiology Reports 3, pp. 10-17 (2001).
Völkel et al., *Targeting of immunoliposomes to endothelial cells using a single -chain Fv fragment directed against human endoglin(CD105)*, Biochemica et Biophysica Acta 1663, pp. 158-166 (2004).
Yau et al. Modern Size-Exclusion Liquid Chromatography, Wiley-Interscience Publication, (1979).
International Search Report for PCT/US2005/030065 filed Aug. 23, 2005, mailed May 23, 2006, 15 pgs.

\* cited by examiner

COMPOSITIONS CONTAINING FAST-LEACHING PLASTICIZERS FOR IMPROVED PERFORMANCE OF MEDICAL DEVICES

BACKGROUND

1. Field of the Invention

This invention relates to a medical implant containing a temporary plasticizer. More particularly, this invention relates to stents containing temporary plasticizers and their methods of use.

2. Description of the State of the Art

Many medical implants undergo a great deal of strain during their manufacture and use that can result in structural failure. Structural failure can occur as a result of manipulating the implant in preparation for placing the implant in a subject and while placing the implant in a desired location in a subject. An example of such a medical implant is a stent. Stents can be used to properly hold open and, if desired, expand a passageway within a subject. Typically, a stent may be compressed, inserted into a small vessel through a catheter, and then expanded to a larger diameter in a subject.

Stent placement can serve as an important step in a variety of medical procedures such as, for example, percutaneous transluminal coronary angioplasty (PTCA)—a procedure used to treat heart disease. In PTCA, a balloon catheter is inserted through a brachial or femoral artery, positioned across a coronary artery occlusion, inflated to compress against atherosclerotic plaque to remodel the lumen of the coronary artery, deflated and withdrawn from the patient. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical by-pass operation. Stents are generally implanted after a PTCA to reduce occlusions, inhibit thrombosis and restenosis, and maintain patency within the lumen of the coronary artery. Examples of patents disclosing stents include U.S. Pat. Nos. 4,733,665, 4,800,882 and 4,886,062.

The manifestation of structural failure in a stent can be a formation of cracks in high-strain areas of the stent such as, for example, in the curved and intersecting regions that are extended during radial expansion of the stent from a compressed form during placement of a stent. As a result, structural failure can occur during placement of the stent in a subject and thereby affect stent performance. Accordingly, manufacturers of medical implants would benefit from new materials that can be highly strained in critical regions of the implant such as, for example, in the loop regions of a stent. These new materials can be used to form implants that can be highly strained during placement in a subject without structural failure and then become sufficiently rigid after placement such that the complications arising from structural implant failure become a thing of the past.

SUMMARY

Medical implants comprising a temporary plasticizer, and their methods of use, are provided. In one embodiment, the invention provides a medical article, wherein the medical article comprises an implant that includes a polymeric material. The polymeric material comprises a plasticizing agent capable of sufficiently increasing a strain-to-failure in the polymeric material to prevent or reduce a formation of cracks in the polymeric material while placing the implant in a subject. The plasticizing agent leaches from the polymeric material after placing the implant in a subject to provide a sufficient rigidity in the polymeric material, and the leaching occurs in less than an amount of time necessary for a required dimension of the implant to change substantially in response to a stress.

In another embodiment, a method of treating a disease in a subject, or ameliorating one or more symptoms thereof is provided. The method includes placing an implant that includes a polymeric material in a subject, wherein the polymeric material comprises a plasticizing agent capable of sufficiently increasing a strain-to-failure in the polymeric material to prevent a formation of cracks in the polymeric material while placing the implant in a subject. The plasticizing agent leaches from the polymeric material after placing the implant in the subject to provide a sufficient rigidity in the polymeric material, and the leaching occurs in less than an amount of time necessary for a required dimension of the implant to change substantially in response to a stress.

In another embodiment, a method of producing a medical article comprising a temporary plasticizing agent is provided. The method comprises combining a polymer with a plasticizing agent capable of sufficiently increasing a strain-to-failure in the polymeric material to prevent or reduce a formation of cracks in the polymeric material while placing an implant in a subject. The plasticizing agent leaches from the polymeric material after placing the implant in the subject to provide a sufficient rigidity in the polymeric material, and the leaching occurs in less than an amount of time necessary for a required dimension of the implant to change substantially in response to a stress.

DETAILED DESCRIPTION

As discussed in more detail below, the invention generally includes a medical article comprising an implant and a method of using the medical article in a subject to treat or ameliorate one or more symptoms of a disease. The term "subject" and "patient" can be used interchangeably in the present invention and refer to an animal such as a mammal including, but not limited to, non-primates such as, for example, a cow, pig, horse, cat, dog, rat and mouse; and primates such as, for example, a monkey or a human.

The implant contains a temporary plasticizer that allows for a high level of strain during placement of the implant in the subject by preventing or reducing a formation of cracks in the implant that would otherwise occur without the temporary plasticizer. The plasticizer is temporary in that it leaches from the implant in less than an amount of time necessary for a required dimension of the implant to change substantially in response to a stress, thus leaving an implant in a subject that is sufficiently rigid for its intended purpose. A change in a required dimension is "substantial" when it has occurred to a degree that significantly affects the clinical utility of a medical device or is more than what may be considered acceptable to one having ordinary skill in the art. In a stent, for example, a required dimension is the diameter of the stent, and a reduction in the diameter of the stent is substantial when it significantly affects the ability of the stent to physically hold open, or expand, the lumen of an organ in a subject. Alternatively, the reduction in the diameter of the stent is "substantial" when the reduction is more than the acceptable standard in the art or the stent is no longer considered as being effective for the procedure for which it was used.

In some embodiments, a change in a required dimension is substantial when the change occurs in an amount ranging from about 0.01% to about 50%, from about 0.1% to about 40%, from about 0.2% to about 30%, from about 0.3% to about 25%, from about 0.5% to about 20%, from about 1% to about 10%, or any range therein. In some embodiments, the implant comprises a stent or a vena cava filter, and the required dimension is a diameter of the stent or vena cava filter following deployment of the stent or vena cava filter in a subject. In these embodiments, the change in the required dimension is a reduction in the diameter of the stent or vena cava filter ranging from about 0.1% to about 20%, from about 1% to about 20%, from about 3% to about 20%, from about 5% to about 20%, from about 0.5% to about 15%, from about 1% to about 10%, or any range therein.

The medical articles provided by the present invention provide a method of treating a disease in a subject, or ameliorating one or more symptoms thereof that are associated with the disease. The term "treating" refers to the placement of a medical implant that contains one or more diagnostic, therapeutic or prophylactic agents.

Figure 1A:
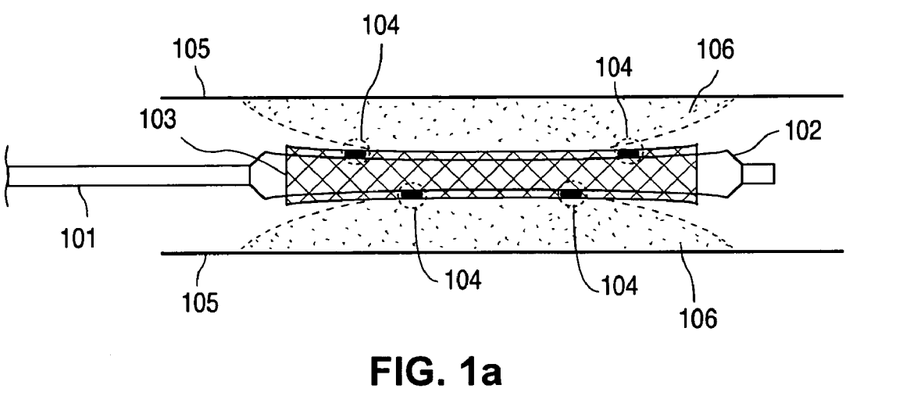
FIGS. 1a–1c illustrate a method for delivering a stent according to embodiments of the present invention.
Figure 1B:
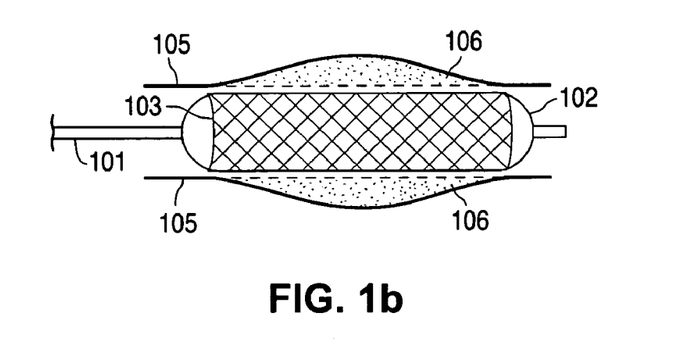
Figure 1C:
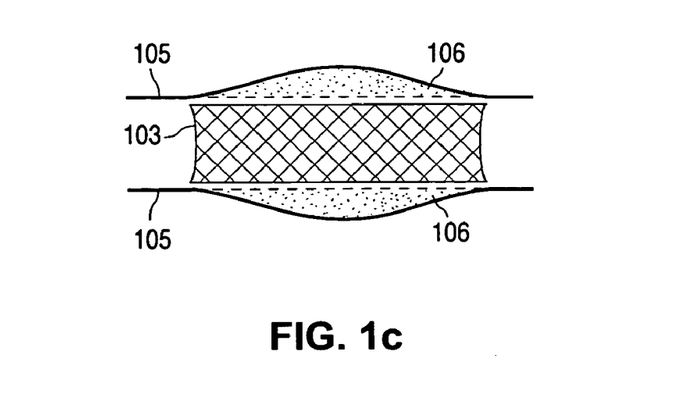

FIGS. 1a–1c illustrate a method for delivering a stent according to embodiments of the present invention. In FIG. 1a, a medical assembly having a catheter body 101, a balloon 102, and a stent 103 having loop regions 104 is positioned in a vascular organ 105. The vascular organ 105 has a lumen that is constricted by the presence of a vascular lesion 106. In FIG. 1b, the balloon 102 is inflated to compress against the vascular lesion 106 to remodel the vascular organ 105 and increase the diameter of the lumen of vascular organ 105. Concurrently, loop regions 104 are subject to a high level of strain during the inflation of balloon 102. As the balloon 102 is inflated, the stent 103 is subject to stress and strain in its expansion and release from the balloon 102. In FIG. 1c, the balloon 102 has been deflated and withdrawn from the vascular organ 105 to complete delivery of the stent 103 in the region of the vascular lesion 106, wherein the stent 103 acts as a rigid structure to properly hold open and, if desired, expand the lumen of vascular organ 105.

Figure 2:
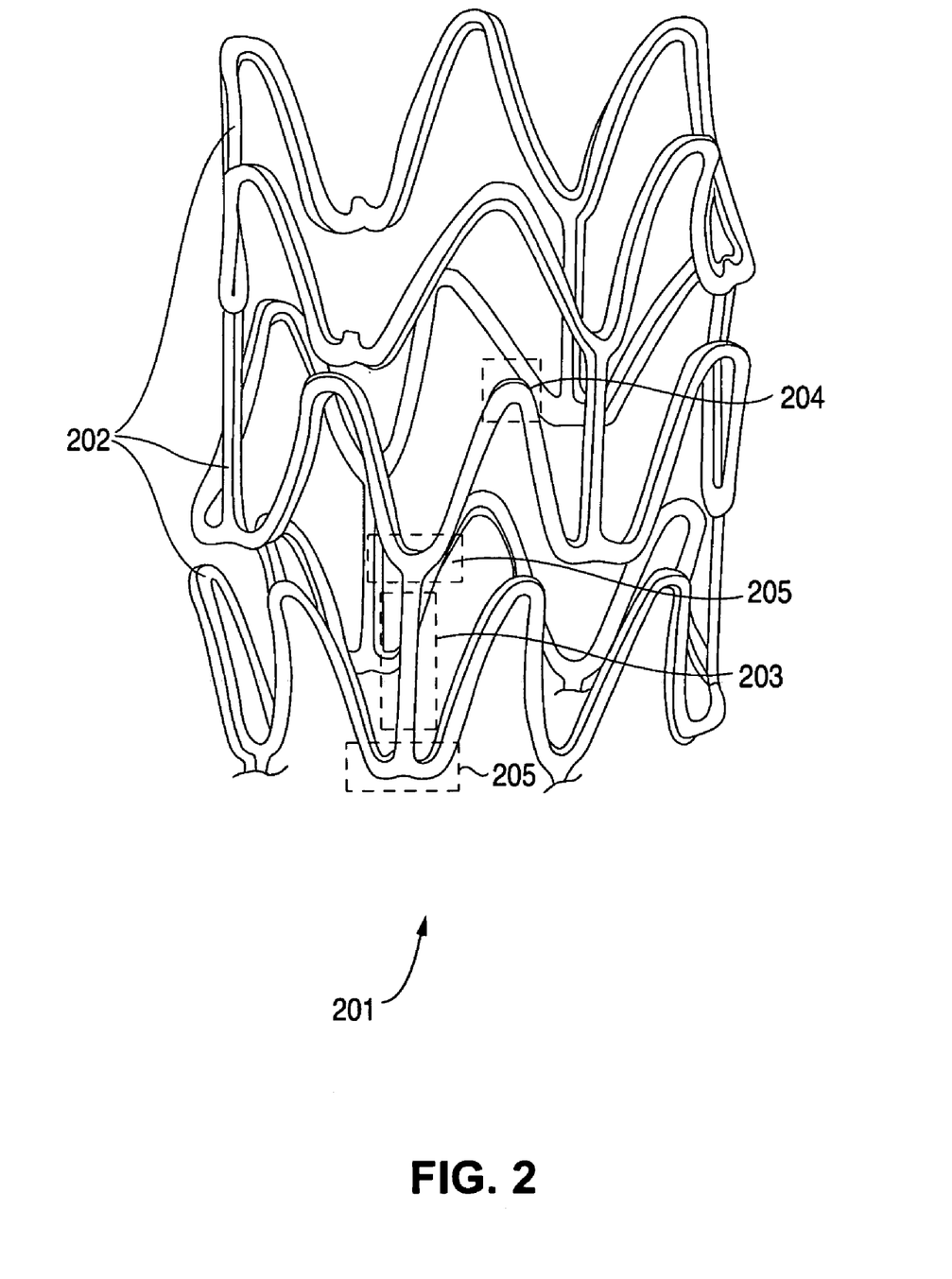
FIG. 2 illustrates a portion of a stent structure to show variations in strain regions according to embodiments of the present invention.

FIG. 2 illustrates a portion of a stent structure to show variations in strain regions according to embodiments of the present invention. In FIG. 2, a design and configuration of a stent 201 is provided for example only and is in no way intended to limit the scope of the present invention. Stent 201 may include a number of interconnecting elements or struts 202, the geometry or shape of which may vary throughout such a stent. General types of struts 202 can include straight struts 203, curved struts 204, and intersecting struts 205. Each of these struts are isolated regions that are subject to stress upon compression and expansion of the stent 201 during, for example, either manufacture or placement of the stent 201 in a subject. The design and configuration of the stent 201 allows for a radial compression during manufacture and a radial expansion during placement, but radial rigidity is also desired for withstanding the stresses associated with holding a body lumen open.

The stress and strain experienced by a medical implant during manufacture and placement in a subject is not uniform throughout the implant such as, for example, during radial compression and expansion. There can be a nonuniformity of stress and strain that can occur during any manipulation of the stent such as, for example, during compression of the stent onto a balloon catheter in preparation for delivery or during expansion of the stent by the balloon catheter during delivery of the stent into an organ. Some portions of a stent pattern may experience little to no strain, whereas others may have a relatively high level of strain. For example, the straight struts 203 experience little to no strain during radial compression and expansion, whereas curved struts 204 and intersecting struts 205 experience relatively high-strain during radial compression and expansion.

Figure 3A:
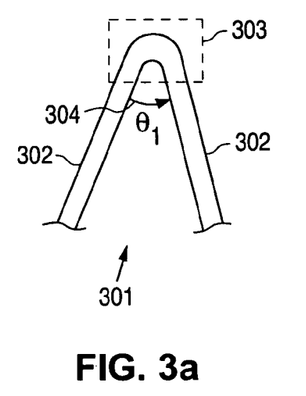
FIGS. 3a–3c illustrate the nonuniformity of stress and strain in curved struts of a stent.
Figure 3B:
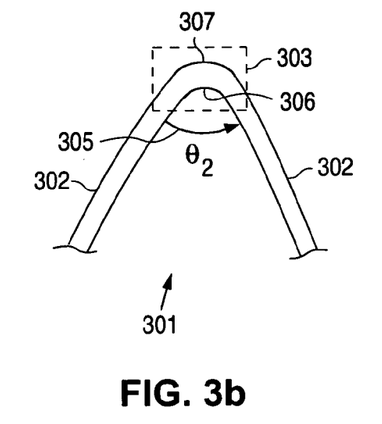
Figure 3C:
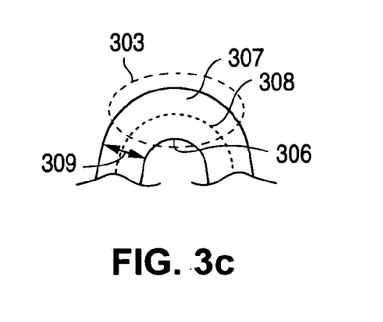

FIGS. 3a–3c illustrate the nonuniformity of stress and strain in curved struts of a stent. FIG. 3a illustrates a curved strut 301 in the stent 201 in an unexpanded state that includes straight sections 302 and curved sections 303 with an angle $\theta_1$ 304. Radial expansion of the stent 201 results in an increase of angle $\theta_1$ 304 between straight sections 302 to angle $\theta_2$ 305, as shown in FIG. 3b. FIGS. 3a and 3b illustrate the curved strut 301 in a plane of bending, which causes little to no strain in straight sections 302 and relatively high levels of stress and strain in most of curved section 303. During radial expansion of the stent, a concave portion 306 of the curved section 303 experiences relatively high tensile stress and strain and a convex portion 307 of the curved section 303 experiences relatively high compressive strain. FIG. 3c illustrates an expanded view of the curve in the curved section 303 and indicates a neutral axis 308 having little to no strain and being positioned along a center of a latitudinal width 309 of the curved section 303.

Figure 4A:
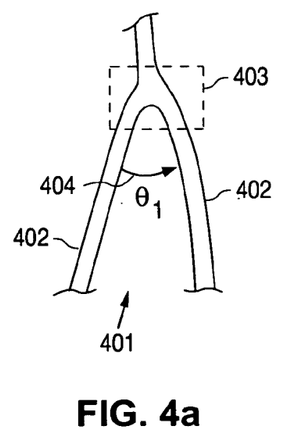
FIGS. 4a and 4b illustrate the nonuniformity of stress and strain in intersecting struts of a stent.
Figure 4B:
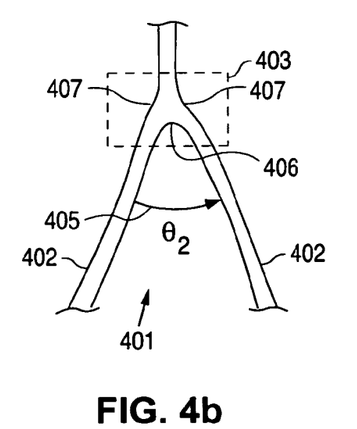

FIGS. 4a and 4b illustrate the nonuniformity of stress and strain in intersecting struts of a stent. FIG. 4a illustrates an intersecting strut 401 in the stent 201 in an unexpanded state that includes straight sections 402 and intersection 403 with an angle $\theta_1$ 404. Radial expansion of stent 201 results in an increase of angle $\theta_1$ 404 between straight sections 402 to angle $\theta_2$ 405, as shown in FIG. 4b. FIGS. 4a and 4b illustrate an intersecting strut 401 in a plane of bending, which causes little to no strain in the straight sections 402 and relatively high levels of stress and strain in most of the intersections 403. During radial expansion, a first concave portion 406 of the curved section 403 experiences relatively high tensile stress and strain and a second concave portion 407 of the curved section 403 experiences relatively high compressive strain.

Figure 5:
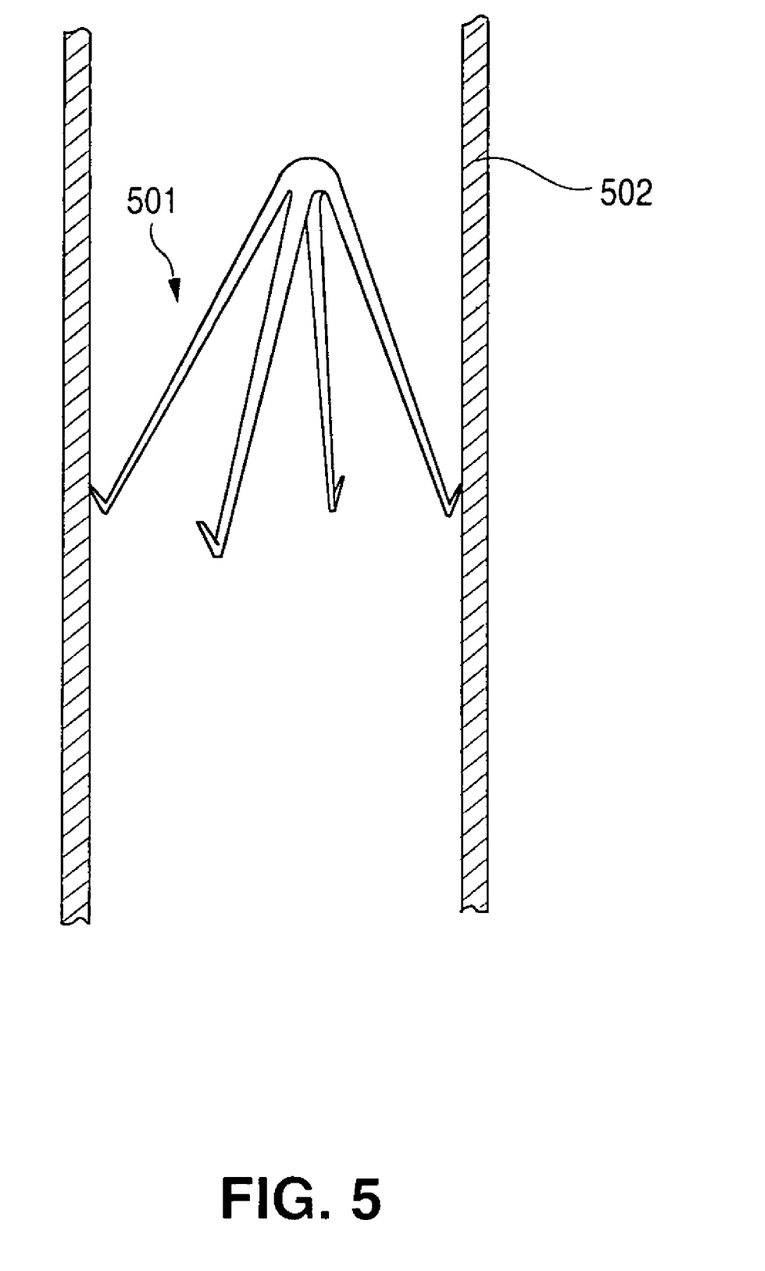
FIG. 5 illustrates a vena cava filter positioned within a vein.

FIG. 5 depicts a vena cava filter 501 typical of the prior art shown positioned inside a vein 502.

It is to be appreciated that the descriptions and analyses of the stress and strain provided herein are not intended to be limiting. Such descriptions and analyses are merely provided to illustrate general concepts and methodology of the invention as it may apply to particular embodiments such as, for example, some stent applications.

Structural failure of a stent can be manifested in a formation of cracks in high-strain areas of the stent such as, for example, in the curved section 303 and the intersections 403 that are extended during radial expansion from a compressed form during placement of the stent 201 in a subject. As a result, structural failure can occur during placement of the stent 201 in a subject and, accordingly, affects stent performance.

In some embodiments, a medical implant comprising a polymeric material and a plasticizing agent that is capable of sufficiently increasing a strain-to-failure in the polymeric material. The term "strain-to-failure" refers to the total strain that can be experienced by a polymeric material before the structure of the polymeric material fails such that it is no longer capable of performing its intended function, or the failure is a result of a damage that is greater than an acceptable standard known to one of skill in the art. For example, the strain-to-failure of a stent can be the amount of strain that a stent can experience prior to failure in a high-strain region of the stent.

In some embodiments, the strain-to-failure can be measured in a laboratory, for example, using a tensile test. A "tensile test" is a measure of the force required to break a specimen of a material and is typically used to produce a stress-strain relationship that can be used to determine the tensile modulus of a material. However, the measure can also identify the point at which the material will fail when subject to strain. Since the physical properties of a material can vary with temperature, a material should be tested at the temperature of the environment in which it will be stressed. In other embodiments, the strain-to-failure can be determined using an empirical approach such as a finite element analysis (FEA), which can be used to calculate the maximum strain in high-strain regions of polymers.

In some embodiments, the medical implant is a stent, and the strain-to-failure of the stent is the amount of strain that can be experienced by the stent before the stent can no longer properly hold open and, if desired, expand a passageway within a subject. In other embodiments, the stent fails due to cracks and/or breaks in the high-strain regions of the stent. In these embodiments, the plasticizing agent can, inter alia, prevent a formation of cracks in the polymeric material that otherwise may occur while placing the implant in a subject, wherein the plasticizing agent leaches from the polymeric material after placing the implant in the subject to provide an implant that is sufficiently rigid to perform its intended function. In other embodiments, the plasticizer leaches from the implant in less than an amount of time necessary for a required dimension of the implant to change substantially in response to a stress such as, for example, the stress placed on a stent by the walls of a lumen that is being held open and/or expanded by the stent.

Placement of an implant in a subject can require a manipulation of the implant to an extent that may result in failure of the implant due to the strain of the manipulation. In some embodiments, the implant comprises a component that can be expanded mechanically. In these embodiments, some components can be expanded with a balloon such as, for example, the expansion of a stent with a balloon catheter. In other embodiments, some components can self-expand while placing the implant in a subject, wherein the self-expansion may occur, for example, as a stent or vena cava filter is forced out of a delivery device (e.g., a catheter) and into a lumen of a subject.

A stent can be used to treat a disease within a subject and can resemble a tube-like body that may be used to open a lumen within an organ in the subject, maintain lumen patency, or reduce the likelihood that the lumen will narrow again. Diseases can be present in a variety of organs within a patient. Examples of such organs include, but are not limited to, vascular organs such as, for example, coronary arteries and hepatic veins; renal organs such as, for example, urethras and ureters; biliary organs such as, for example, biliary ducts; pulmonary organs such as, for example, tracheas, bronchi and bronchioles; and gastrointestinal organs such as, for example, esophagi and colons, to name a few. Stents can be used to treat and/or ameliorate one or more symptoms of a variety of diseases that include, but are not limited to, atherosclerosis, benign prostatic hypertrophy, recoiling lesions after percutaneous transluminal angioplasty and in dissections, chronic occlusions, anastamotic hyperplasia in vein grafts and synthetic vascular grafts, vulnerable plaque, aneurysms of the aorta and large arteries, arteriovenous fistulae and traumatic leaks, malignant stenosis of the gastrointestinal tract, acute ileus in colorectal cancer, biliary closure from cholangiocarcinoma or other hepatic cancers, benign compression of the trachea and malignant tracheobronchial obstructions.

A stent can be composed of any materials and have any dimensions known to be useful to one of skill in the art. In some embodiments, the stents include, but are not limited to, tubular stents, self-expanding stents, coil stents, ring stents, multi-design stents, and the like. In other embodiments, the stents are metallic; low-ferromagnetic; non-ferromagnetic; biostable polymeric; biodegradable polymeric or biodegradable metallic. In some embodiments, the stents are coated such as, for example, with a polymer containing a drug. A coating can be exclusively on the outer surface, exclusively on the inner surface, or on both the outer surface and the inner surface of the stent.

A stent can be composed of a metal, an alloy, a polymer, or a combination thereof. Examples of materials used to form stents include, but are not limited to, ELASTINITE® (Guidant Corp.), NITINOL (Nitinol Devices and Components), stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (ELGILOY®, Elgiloy Specialty Metals, Inc.; MP35N and MP20N, SPS Technologies), and combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum.

Since stents can be placed in a variety of organs within a subject, stents can have a variety of dimensions. In some embodiments, the diameter of the stent can range from about 0.025 mm to about 50 mm, from about 0.05 mm to about 25 mm, from about 0.1 mm to about 20 mm, from about 0.25 mm to about 15 mm, from about 0.50 mm to about 10 mm, from about 1.0 mm to about 5 mm, or any range therein. In other embodiments, the diameter of the stent can range from about 0.05 mm to about 2.5 mm, from about 0.10 mm to about 2.0 mm, from about 0.25 mm to about 1.5 mm, from about 0.50 mm to about 1.0 mm, or any range therein. In other embodiments, the diameter of the stent can range from about 10 mm to about 25 mm, from about 12 mm to about 22 mm, from about 15 mm to about 20 mm, or any range therein. In some embodiments, the length of the stent can range from about 0.1 mm to about 100 mm, from about 0.5 mm to about 75 mm, from about 1.0 mm to about 60 mm, from about 2.0 mm to about 60 mm, from about 4.0 mm to about 60 mm, from about 1.0 mm to about 50 mm, from about 5.0 mm to about 50 mm, from about 1.5 mm to about 40 mm, from about 2.0 mm to about 30 mm, or any range therein.

The medical articles of the present invention can be formed using bioabsorbable polymers, biostable polymers or a combination thereof. For the purposes of the present invention, a polymer or coating is "bioabsorbable" or "biodegradable" when it is capable of being completely or substantially degraded or eroded when exposed to either an in vivo environment or an in vitro environment having physical, chemical, or biological characteristics substantially similar to those of the in vivo environment within a subject. A polymer or coating is "degradable or erodable" when it can be gradually broken-down, resorbed, absorbed and eliminated by, for example, hydrolysis, enzymolysis, metabolic processes, bulk or surface erosion, and the like within a subject. It should be appreciated that traces or residue of polymer may remain following biodegradation. The terms "bioabsorbable," "biodegradable," and "bioerodable" are used interchangeably in this application. A "biostable" polymer is a polymer that is not bioabsorbable.

The polymers used in the present invention can be hydrophobic, hydrophilic, amphiphilic, biodegradable, or a combination thereof. Examples of hydrophobic polymers include, but are not limited to, poly(ester amide), polystyrene-polyisobutylene-polystyrene block copolymer (SIS), polystyrene, polyisobutylene, polycaprolactone (PCL), poly (L-lactide), poly(D,L-lactide), polylactic acid (PLA), poly (lactide-co-glycolide), poly(glycolide), polyalkylene, polyfluoroalkylene, polyhydroxyalkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hyroxyhexanoate), mid-chain polyhydroxyalkanoate, poly (trimethylene carbonate), poly(orthoester), polyphosphazenes, poly(phosphoester), poly(tyrosine derived arylates), poly(tyrosine derived carbonates), polydimethyloxanone (PDMS), polyvinylidene fluoride (PVDF), polyhexafluoropropylene (HFP), polydimethylsiloxane, poly(vinylidene fluoride-co-hexafluoropropylene) (PVDF-HFP), poly(vinylidene fluoride-co-chlorotrifluoroethylene) (PVDF-CTFE), poly(butyl methacrylate), poly(methyl methacrylate), poly(methacrylates), poly(vinyl acetate), poly(ethylene-co-vinyl acetate), poly(ethylene-co-vinyl alcohol), poly(ester urethanes), poly(ether-urethanes), poly (carbonate-urethanes), poly(silicone-urethanes), poly(2-hydroxyethyl methacrylate), Solef® PVDF (polyvinylidene fluoride), poly(urea-urethanes), and combinations thereof.

Examples of hydrophilic polymers include, but are not limited to, polymers and co-polymers of carboxyl and hydroxyl bearing monomers including, but not limited to, hydroxylethyl methacrylate (HEMA), hydroxypropyl methacrylate (HPMA), hydroxypropylmethacrylamide, alkoxymethacrylate, alkoxyacrylate, and 3-trimethylsilylpropyl methacrylate (TMSPMA), poly(methyl methacrylate) (PMMA), poly(ethylene glycol) (PEG), poly(propylene glycol) (PPG), PEG acrylate (PEGA), PEG methacrylate, methacrylic acid (MA), ethylene-vinyl acetate, acrylic acid (AA), SIS-PEG, polystyrene-PEG, polyisobutylene-PEG, PCL-PEG, PLA-PEG, PMMA-PEG, PDMS-PEG, PVDF-PEG, PLURONIC™ surfactants (polypropylene oxide-co-polyethylene glycol), poly(tetramethylene glycol), phosphorylcholine, 2-methacryloyloxyethyl phosphorylcholine (MPC), n-vinyl pyrrolidone (VP), hydroxy functional poly (vinyl pyrrolidone), polyalkylene oxide, dextran, dextrin, sodium hyaluronate, hyaluronic acid, heparin, elastin, chitosan, and combinations thereof.

Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, or combinations thereof. In some embodiments, the biodegradable polymers include, but are not limited to, polyesters, polyhydroxyalkanoates (PHAs), poly(ester amides); amino acids; PEG and/or alcohol groups, polycaprolactones, poly(L-lactide), poly(D,L-lactide), poly(D,L-lactide-co-PEG) block copolymers, poly (D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g., PEO/PLA), polyalkylene oxalates, polyphosphazenes, PHA-PEG, and any derivatives, analogs, homologues, salts, copolymers and combinations thereof.

In other embodiments, the biodegradable polymers may include, but are not limited to, PHAs such as, for example, poly(α-hydroxyacids); poly(β-hydroxyacids) such as poly (3-hydroxybutyrate) (PHB); poly(3-hydroxybutyrate-co-valerate) (PHBV); poly(3-hydroxyproprionate) (PHP); poly (3-hydroxyhexanoate) (PHH); a poly(4-hydroxyacid) such as poly(4-hydroxybutyrate), poly(4-hydroxyvalerate), or poly(4-hydroxyhexanoate); poly(hydroxyvalerate); and any derivatives, analogs, homologues, salts, copolymers and combinations thereof. In other embodiments, the biodegradabe polymers include, but are not limited to, polyanhydrides, poly(hydroxyethyl methacylate), poly(N-acylhydroxyproline)esters, poly(N-palmitoyl hydroxyproline)esters, polyphosphazenes, poly(tyrosine carbonates), poly(tyrosine arylates), and any derivatives, analogs, homologues, salts, copolymers and combinations thereof.

It should also be appreciated that, in some embodiments, one of skill in the art may select one or more particular polymers in order to exclude any one or any combination of the above-described polymers.

Agents

The medical articles of the present invention can comprise an agent. In one embodiment, the agent can be included in the body of a medical article such as, for example, a biodegradable polymeric stent. In another embodiment, the agent can be included in a coating for a medical article. An "agent" is a moiety that may be biobeneficial, bioactive, diagnostic, plasticizing, or a combination thereof. A "moiety" includes, but is not limited to, functional groups composed of at least 1 atom, bonded residues in a macromolecule, individual units in a copolymer and entire polymeric blocks.

Bioactive and Biobeneficial Agents

A "bioactive agent" is a moiety that is mixed, blended, bonded or linked to a polymer coating, or to a polymer from which a stent is made, and provides a therapeutic effect, a prophylactic effect, both a therapeutic and a prophylactic effect, or other biologically active effect upon release from the stent. The bioactive agents of the present invention may remain linked to a portion of the polymer or be released from the polymer. A "biobeneficial agent" is an agent that can be mixed, blended, bonded or linked to a polymer that provides a biological benefit within a subject without necessarily being released from the stent. The terms "plasticizer" and "plasticizing agent" are described in more detail below and include any agent that can be added to a polymeric composition to modify its mechanical properties or the mechanical properties of a product formed from the polymeric composition.

A "diagnostic agent" can be a type of bioactive or biobeneficial agent that can be used, for example, in diagnosing the presence, nature, and/or extent of a disease or medical condition in a subject. In one embodiment, a diagnostic agent can be any agent which may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, radiofrequency (RF) and microwave laser. Diagnostic agents may also include any other agents useful in facilitating diagnosis of a disease or other condition in a patient, whether or not imaging methodology is employed.

Biobeneficial agents are moieties that may be mixed, blended, bonded or linked to a polymer and are capable of providing a biological benefit such as, for example, control of protein adsorption on an implant surface, without being released from the polymer. Biobeneficial agents can have a reactive group that can be used to link the agent to a polymer. Examples of reactive groups include, but are not limited to, hydroxyl, carboxyl, and amino groups. In some embodiments, the molecular weight of the agent should be at or below about 40,000 Daltons, or any range therein, to ensure elimination of the agent from a subject. In one embodiment, the molecular weight of the agent ranges from about 300 Daltons to about 40,000 Daltons, from about 8,000 Daltons to about 30,000 Daltons, from about 10,000 Daltons to about 20,000 Daltons, or any range therein.

Examples of biobeneficial agents include, but are not limited to, poly(alkylene glycols), poly(N-vinyl pyrrolidone), poly(acrylamide methyl propane sulfonic acid), poly(styrene sulfonate), sulfonated dextran, polyphosphazenes, poly(orthoesters), poly(tyrosine carbonate), hyaluronic acid, heparin and any derivatives, analogs, homologues, congeners, salts, copolymers and combinations thereof. It is to be appreciated that one skilled in the art should recognize that some of the groups, subgroups, and individual biobeneficial agents may not be used in some embodiments of the present invention.

The poly(alkylene glycols) include, but are not limited to, PEG, methoxy poly(ethylene glycol) (mPEG), poly(ethylene oxide), PPG, poly(tetramethylene glycol), poly(ethylene oxide-co-propylene oxide) and any derivatives, analogs, homologues, congeners, salts, copolymers and combinations thereof. In one embodiment, the poly(alkylene glycol) is mPEG. In some embodiments, the PEGs can have molecular weights ranging from about 400 Daltons to about 30,000 Daltons, from about 400 Daltons to about 25,000 Daltons, from about 400 Daltons to about 20,000 Daltons, from about 400 Daltons to about 15,000 Daltons, from about 500 Daltons to about 10,000 Daltons, from about 750 Daltons to about 7500 Daltons, from about 1000 Daltons to about 10,000 Daltons, from about 1000 Daltons to about 5000 Daltons, or any range therein.

The copolymers that may be used as biobeneficial agents include, but are not limited to, any derivatives, analogs, homologues, congeners, salts, copolymers and combinations of the foregoing examples of biobeneficial agents. Examples of copolymers that may be used as biobeneficial agents in the present invention include, but are not limited to, copolymers of PEG and hyaluronic acid; copolymers of PEG and heparin; graft copolymers of poly(L-lysine) and PEG; and, any derivative, analog, congener, salt, or combination thereof, of the copolymers. In one embodiment, the copolymer that may be used as a biobeneficial agent is a copolymer of PEG and hyaluronic acid, or any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a subject. The bioactive agents include, but are not limited to, small molecules, nucleotides, oligonucleotides, polynucleotides, nucleic acids, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin $I_1$, actinomycin $X_1$, actinomycin $C_1$, and dactinomycin (COSMEGEN®, Merck & Co., Inc.).

Antineoplastics or antimitotics include, for example, paclitaxel (TAXOL®, Bristol-Myers Squibb Co.), docetaxel (TAXOTERE®, Aventis S.A.), docetaxel, methotrexate, azathioprine, vincristine, vinblastine, fluorouracil, doxorubicin hydrochloride (ADRIAMYCIN®, Pfizer, Inc.) and mitomycin (MUTAMYCIN®, Bristol-Myers Squibb Co.), and any prodrugs, metabolites, analogs, homologues, congeners, derivatives, salts and combinations thereof. Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX®, Biogen, Inc.), and any prodrugs, metabolites, analogs, homologues, congeners, derivatives, salts and combinations thereof. Cytostatic or antiproliferative agents include, for example, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof. Antiallergic agents include, but are not limited to, pemirolast potassium (ALAMAST®, Santen, Inc.), and any prodrugs, metabolites, analogs, homologues, congeners, derivatives, salts and combinations thereof.

Other bioactive agents useful in the present invention include, but are not limited to, free radical scavengers; nitric oxide donors; rapamycin; methyl rapamycin; everolimus; tacrolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells including, but not limited to prokaryotes and eukaryotes such as, for example, epithelial cells and genetically engineered epithelial cells; dexamethasone; and, any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate, and any analogs, homologues, congeners, derivatives, salts and combinations thereof.

Examples of diagnostic agents include radioopaque materials and include, but are not limited to, materials comprising iodine or iodine-derivatives such as, for example, iohexal and iopamidol, which are detectable by x-rays. Other diagnostic agents such as, for example, radioisotopes, are detectable by tracing radioactive emissions. Other diagnostic agents may include those that are detectable by magnetic resonance imaging (MRI), ultrasound and other imaging procedures such as, for example, fluorescence and positron emission tomagraphy (PET). Examples of agents detectable by MRI are paramagnetic agents, which include, but are not limited to, gadolinium chelated compounds. Examples of agents detectable by ultrasound include, but are not limited to, perflexane. Examples of fluorescence agents include, but are not limited to, indocyanine green. Examples of agents used in diagnostic PET include, but are not limited to, fluorodeoxyglucose, sodium fluoride, methionine, choline, deoxyglucose, butanol, raclopride, spiperone, bromospiperone, carfentanil, and flumazenil.

It should be appreciated that the agents of the present invention can have both biobeneficial and bioactive properties, and that classification of an agent as a biobeneficial agent does not preclude the use of that agent as a bioactive agent. Likewise, classification of an agent as a bioactive agent does not preclude the use of that agent as a biobeneficial agent. It should also be appreciated that, in some embodiments, one of skill in the art may select one or more particular agents in order to exclude any one or any combination of the above-described agents.

Plasticizing Agents

The terms "plasticizer" and "plasticizing agent" can be used interchangeably in the present invention and can include any bioactive, biobeneficial or diagnostic agent described above. A plasticizing agent can include any agent or combination of agents that can be added to modify the mechanical properties of a polymeric composition or a product formed from the polymeric composition.

Without intending to be bound by any theory or mechanism of action, plasticizers can be added, for example, to reduce crystallinity, lower the glass-transition temperature ($T_g$), or reduce the intermolecular forces between polymers, with a design goal that may include creating or enhancing a flow between polymers in the composition. The mechanical properties that are modified include, but are not limited to, Young's modulus, tensile strength, impact strength, tear strength, and strain-to-failure. A plasticizer can be monomeric, polymeric, co-polymeric, or a combination thereof, and can be added to a polymeric composition with or without covalent bonding. Plasticization and solubility are analogous to the extent that selecting a plasticizer involves considerations similar to the considerations in selecting a solvent such as, for example, polarity. Furthermore, plasticizers can also be added to a polymeric composition through covalent bonding that changes the molecular structure of the polymer through copolymerization.

Examples of plasticizing agents include, but are not limited to, low molecular weight polymers such as, for example, single-block polymers, multi-block polymers, and copolymers; oligomers such as, for example, lactic acid oligomers including, but not limited to, ethyl-terminated oligomers of lactic acid; dimers of cyclic lactic acid and glycolic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; saturated and unsaturated fatty acids; fatty alcohols; cholesterol; steroids; phospholipids such as, for example, lecithin; proteins such as animal proteins and vegetable proteins; oils such as, for example, the vegetable oils and animal oils; silicones; acetylated monoglycerides; diglycerides; triglycerides; amides; acetamides; sulfoxides; sulfones; pyrrolidones; oxa acids; diglycolic acids; and any analogs, derivatives, copolymers and combinations thereof.

In some embodiments, the plasticizers include, but are not limited to other polyols such as, for example, caprolactone diol, caprolactone triol, sorbitol, erythritol, glucidol, mannitol, sorbitol, sucrose, and trimethylol propane. In other embodiments, the plasticizers include, but are not limited to, glycols such as, for example, ethylene glycol, diethylene glycol, triethylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In other embodiments, the plasticizers include, but are not limited to esters such as glycol esters such as, for example, diethylene glycol dibenzoate, dipropylene glycol dibenzoate, triethylene glycol caprate-caprylate; monostearates such as, for example, glycerol monostearate; citrate esters; organic acid esters; aromatic carboxylic esters; aliphatic dicarboxylic esters; fatty acid esters such as, for example, stearic, oleic, myristic, palmitic, and sebacic acid esters; triacetin; poly(esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate; sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxyethoxyethyl adipate, diisobutyl adipate, sebacic esters, azelaic esters, citric esters, and tartaric esters; and fatty acid esters such as, for example, glycerol, mono- di- or triacetate, and sodium diethyl sulfosuccinate; and any analogs, derivatives, copolymers and combinations thereof.

In other embodiments, the plasticizers include, but are not limited to ethers and polyethers such as, for example, poly(alkylene glycols) such as poly(ethylene glycols) (PEG), poly(propylene glycols), and poly(ethylene/propylene glycols); PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

The term "low molecular weight polymers" refers to agents that can be combined with a water-containing solvent or a lipid-containing solvent at temperatures that range from about room temperature to about the body temperature of subject to form a liquid or semi-solid. In some embodiments, such a low molecular weight polymeric material can be any polymer that can dissolve in a limited amount of water and leach from a polymeric material. In other embodiments, such a low molecular weight polymeric material can be any polymer that can dissolve in a bodily fluid. The molecular weight of such a polymer will vary, and the structure of the polymer will guide one skilled in the art in the determination of the appropriate molecular weight to use in a particular application.

In other embodiments, the plasticizers include, but are not limited to, amides such as, for example, oleic amide, erucic amide, and palmitic amide; alkyl acetamides such as, for example, dimethyl acetamide; sulfoxides such as for example, dimethyl sulfoxide; pyrrolidones such as, for example, n-methyl pyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof In other embodiments, the plasticizers include, but are not limited to vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid; essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, cassia oil, chenopodium oil, chrysanthemum oil, cinae aetheroleum, citronella oil, lemon oil, citrus oil, costus oil, curcuma oil, carlina oil, elemi oil, tarragon oil, eucalyptus oil, fennel oil, pine needle oil, pine oil, filicis, aetheroleum, galbanum oil, gaultheriae aetheroleum, geranium oil, guaiac wood oil, hazelwort oil, iris oil, hypericum oil, calamus oil, camomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarine oil, melissa oil, menthol, millefolii aetheroleum, mint oil, clary oil, nutmeg oil, spikenard oil, clove oil, neroli oil, niaouli, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, sassafras oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and, any analogs, derivatives, copolymers and combinations thereof.

It should be appreciated that, in some embodiments, one of skill in the art may select one or more particular plasticizing agents in order to exclude any one or any combination of the above-described plasticizing agents.

In some embodiments, the plasticizing agent can include a component that is water-soluble. In other embodiments, the plasticizing agent can be modified to be water-soluble. In some embodiments, the plasticizing agent can include a component that is lipid-soluble. In other embodiments, the plasticizing agent can be modified to be lipid-soluble. Any functional group can be added to modify the plasticizer's behavior in a solvent such as, for example, body fluids that are present in vivo.

In other embodiments, the functional groups can include, but are not limited to, oxygen-containing groups such as, for example, alcohols, ethers, phenols, and derivatives thereof. Such oxygen-containing groups include, but are not limited to, acetonides, alcohols, alkoxides, bisphenols, carbinols, cresols, diols, enols, enolates, epoxides, ethers, glycols, hydroperoxides, peroxides, phenols, phenolates, phenoxides, pinacols, trioxides, and ynols.

In other embodiments, the functional groups can include, but are not limited to, oxygen-containing groups such as, for example, aldehydes, ketones, quinones and derivatives thereof. Such oxygen-containing groups include, but are not limited to, acetals, acyloins, aldehydes, carbonyl compounds, diosphenols, dypnones, hemiacetals, hemiketals, ketals, ketenes, keto compounds, ketones, quinhydrones, quinomethanes, quinines, and combinations thereof.

In other embodiments, the functional groups can include, but are not limited to, oxygen-containing groups such as, for example, carboxylic acids and derivatives thereof. Such oxygen-containing groups include, but are not limited to, carboxylic acids, oxoacids, sulfonic acids, acid anhydrides, acid thioanhydrides, acyl groups, acyl halides, acylals, anhydrides, carboxylic acids, cyclic acid anhydrides, cyclic anhydrides, esters, fulgides, lactides, lactols, lactones, macrolides, naphthenic acids, ortho acids, ortho esters, oxo carboxylic acids, peroxy acids, and combinations thereof.

In other embodiments, the functional groups can include, but are not limited to, nitrogen-containing groups containing one nitrogen such as, for example, aldimines, aldoximes, alkoxyamines, amic acids, amides, amines, amine oxides, amine ylides, carbamates, hemiaminals, carbonitriles, carboxamides, isocyanides, cyanates, isocyanates, diisocyanates, cyanides, cyanohydrins, diacylamines, enamines, fulminates, hemiaminals, hydroxamic acids, hydroximic acids, hydroxylamines, imides, imidic acids, imidines, imines, oximes, isoureas, ketenimines, ketimines, ketoximes, lactams, lactims, nitriles, nitro, nitroso, nitrosolic acids, oxime O-ethers, quaternary ammonium compounds, quinone imines, quinonoximes, azomethines, ureides, urethanes, and combinations thereof.

In other embodiments, the functional groups can include, but are not limited to, nitrogen-containing groups containing two or more nitrogens such as, for example, aldazines, amide hydrazones, amide oximes, amidines, amidrazones, aminals, amine imides, amine imines, isodiazenes, azans, azides, azo imides, azines, azo compounds, azomethine imides, azoxy compounds, carbodiimides, carboxamidines, diamidides, diazo compounds, diazoamino compounds, diazoates, diazooxides, formamidine disulfides, formazans, hydrazides, hydrazide hydrazones, hydrazide imides, hydrazidines, hydrazines, hydrazo compounds, hydrazones, ketazines, nitramines, nitrile imines, nitrimines, nitrolic acids, nitrosamides, nitrosamines, nitrosimines, ortho amides, semicarbazones, semioxamazones, triazanes, triazenes, and combinations thereof.

In other embodiments, the functional groups can include, but are not limited to, sulfur-containing groups such as thio, thiol, thioether, sulfonyl, sulfido, sulfinamides, sulfilimines, sulfimines, sulfimides, sulfinamidines, sulfines, sulfonic acids, sulfinic anhydrides, sulfinylamines, sulfonamides, sulfones, sulfonediimines, sulfonic acids, sulfonic anhydrides, sulfoxides, sulfoximides, and combinations thereof.

In other embodiments, the functional groups can include, but are not limited to, silyl groups; halogens; selenoethers; trifluoromethyls; thio-derivatives of urethanes where at least one oxygen atom is replaced by a sulfur atom; phosphoryls, phosphonates, and phosphinates; and ethyleneically unsaturated groups such as, for example, allyl, acryloyl, methacrylol, maleate and maleimido; and combinations thereof.

In other embodiments, the functional group may include light scattering groups, magnetic groups, nanogold, other proteins, a solid matrix, radiolabels, carbohydrates, and combinations thereof.

The molecular weights of the plasticizers can range from about 10 Daltons to about 100,000 Daltons; from about 25 Daltons to about 50,000 Daltons; from about 50 Daltons to about 25,000 Daltons; from about 100 Daltons to about 10,000 Daltons; from about 200 Daltons to about 7,500 Daltons; from about 500 Daltons to about 5000 Daltons; from about 10 Daltons to about 5000 Daltons; from about 10 Daltons to about 2500 Daltons; from about 10 Daltons to about 2000 Daltons; from about 10 Daltons to about 1750 Daltons; from about 10 Daltons to about 1500 Daltons; from about 10 Daltons to about 1000 Daltons; from about 10

Daltons to about 500 Daltons; under 500 Daltons; and any range therein. In some embodiments, the PEGs have a molecular weight of less than about 1500 Daltons. In other embodiments, the PEGs have a molecular weight ranging from about 400 Daltons to about 600 Daltons and can be obtained by using a mixture of PEGs such as, for example, about a 50/50 mixture of PEG 400 and PEG 800.

In some embodiments, the use of the plasticizing agents of the present invention can increase the strain-to-failure of a material by a factor ranging from about 1.01 to about 100; from about 1.03 to about 100; from about 1.05 to about 100; from about 1.05 to about 50; from about 1.05 to about 30; from about 1.05 to about 25; from about 1.1 to about 20; from about 1.25 to about 20; from about 1.5 to about 20; from about 1.75 to about 20; from about 2 to about 10; from about 2 to about 5; or any range therein.

Concentrations of Agents

The agents of the present invention can have properties that are biobeneficial, bioactive, diagnostic, ameliorative, plasticizing or a combination thereof. For example, classification of an agent as a biobeneficial agent does not preclude the use of that agent as a bioactive agent, diagnostic agent and/or plasticizing agent. Likewise, classification of an agent as a bioactive agent does not preclude the use of that agent as a diagnostic agent, biobeneficial agent and/or plasticizing agent. Furthermore, classification of an agent as a plasticizing agent does not preclude the use of that agent as a biobeneficial agent, bioactive agent, and/or diagnostic agent. Moreover, each agent may also have an ability to ameliorate a symptom of a disease.

It should be appreciated that the plasticizers can be blended, mixed, bonded, or otherwise combined with other active agents to obtain other desired functions such as, for example, an added therapeutic, prophylactic, ameliorative and/or diagnostic function. In some embodiments, the plasticizers can be linked to the polymeric composition or other agents through ether, amide, ester, orthoester, anhydride, ketal, acetal, and all-aromatic carbonate linkages. In these embodiments, an agent such as a plasticizing agent can be designed to hydrolyze in vivo and leach from the polymeric composition at a predetermined rate.

Accordingly, the amounts of the agents that are added to the polymeric compositions can vary according to a variety of factors including, but not limited to, the biological activity of the agent; the age, body weight, response, and the past medical history of the subject; and, the pharmacokinetic and pharmacodynamic effects of the agents or combination of agents. Factors such as these are routinely considered by one of skill in the art. Effective amounts, for example, may be extrapolated from in vitro and/or animal model systems. In some embodiments, the agent or combination of agents have a concentration that ranges from about 0.01% to about 75%; from about 0.05% to about 70%; from about 0.1% to about 60%; from about 0.25% to about 60%; from about 0.5% to about 50%; from about 0.75% to about 40%; from about 1.0% to about 30%; from about 2% to about 20%; and, any range therein, where the percentage is based on the total weight of the polymer and agent or combination of agents.

Agents can be combined to obtain a combination of desired properties and functions in a polymeric material. In some embodiments, a secondary plasticizer can be combined with a primary plasticizer in an amount that ranges from about 0.01% to about 50%; from about 0.05% to about 50%; from about 0.75% to about 50%; from about 1.0% to about 40%; from about 2% to about 30%; from about 1% to about 20%; from about 3% to about 20%; from about 3% to about 10%; or any range therein, as a weight percentage based on the total weight of the plasticizer. In other embodiments, one or more plasticizers may leach from a medical article, and one or more plasticizers may remain, while providing a polymeric material with sufficient rigidity.

Forming a Medical Article

The plasticizing agent can be localized in an implant during a process of forming the implant, and the localization of plasticizer can be beneficial for a variety of reasons such as, for example, use of less plasticizer in select regions; use of a preferred plasticizer in select regions such as, for example, a plasticizer with a lower toxicity or faster leaching rate; modification of mechanical properties of select regions of an implant; leaching of less plasticizer for elimination by a subject; and combinations thereof. In some embodiments, there may be no plasticizer in the regions outside of the high-strain regions in an implant. In other embodiments, there may be less plasticizer in the regions outside of the high-strain regions in an implant. In embodiments where less plasticizer is desired in the regions outside of the high-strain regions, the amount of plasticizer in the regions outside of the high-strain regions can have 2%, 5%, 10%, 15%, 20%, 30%, 40%, 50%, 60%, 70%, 80%, 90%, 95%, or any range therein, less plasticizer than the high-strain regions.

Processes for forming a medical article include, but are not limited to, casting, molding, coating, and combinations thereof. In some embodiments, the implant is formed in a casting process, and the mechanical properties of the high-strain regions of the implant are controlled by concentrating the plasticizer in the high-strain regions, by using different plasticizers in the high-strain regions, by using plasticizer only in the high-strain regions, or a combination thereof. Casting an implant involves pouring a liquid polymeric composition into a mold. In one embodiment, the localization of plasticizer in an implant during such casting can be obtained by varying the amount and/or type of plasticizer in the polymeric composition during pouring as desired such that the plasticizer becomes localized in the formed implant.

In other embodiments, the implant is formed in a molding process, which includes, but is not limited to, compression molding, extrusion molding, injection molding, and foam molding. The mechanical properties of the high-strain regions of the implant are controlled by concentrating the plasticizer in the high-strain regions, by using different plasticizers in the high-strain regions, by using plasticizer only in the high-strain regions, or a combination thereof.

In compression molding, solid polymeric materials are added to a mold and pressure and heat are applied until the polymeric material conforms to the mold. The solid form may require additional processing to obtain the final product in a desired form. The solid polymeric materials can be in the form of particles that can vary in mean diameter from about 1 nm to about 1 cm, from about 1 nm to about 10 mm, from about 1 nm to about 1 mm, from about 1 nm to about 100 nm, or any range therein. In one embodiment, the localization of plasticizer in an implant during such compression molding can be obtained by varying the amount and/or type of plasticizer in the solid polymeric materials while adding the solid polymeric materials to the mold as desired such that the plasticizer becomes localized in the formed implant.

In extrusion molding, solid polymeric materials are added to a continuous melt that is forced through a die and cooled to a solid form. The solid form may require additional processing to obtain the final product in a desired form. The solid polymeric materials can be in the form of particles that can vary in mean diameter from about 1 nm to about 1 cm, from about 1 nm to about 10 mm, from about 1 nm to about 1 mm, from about 1 nm to about 100 nm, or any range therein. In one embodiment, the localization of plasticizer in an implant during such extrusion molding can be obtained by varying the amount and/or type of plasticizer in the solid polymeric materials while adding the solid polymeric materials to the extrusion mold as desired such that the plasticizer becomes localized in the formed implant.

In injection molding, solid polymeric materials are added to a heated cylinder, softened and forced into a mold under pressure to create a solid form. The solid form may require additional processing to obtain the final product in a desired form. The solid polymeric materials can be in the form of particles that can vary in mean diameter from about 1 nm to about 1 cm, from about 1 nm to about 10 mm, from about 1 nm to about 1 mm, from about 1 nm to about 100 nm, or any range therein. In one embodiment, the localization of plasticizer in an implant during such injection molding can be obtained by varying the amount and/or type of plasticizer in the solid polymeric materials while adding the solid polymeric materials to the injection mold as desired such that the plasticizer becomes localized in the formed implant.

In foam molding, blowing agents are used to expand and mold solid polymeric materials into a desired form, and the solid polymeric materials can be expanded to a volume ranging from about two to about 50 times their original volume. The polymeric material can be pre-expanded using steam and air and then formed in a mold with additional steam; or mixed with a gas to form a polymer/gas mixture that is forced into a mold of lower pressure. The solid form may require additional processing to obtain the final product in a desired form. The solid polymeric materials can be in the form of particles that can vary in mean diameter from about 1 nm to about 1 cm, from about 1 nm to about 10 mm, from about 1 nm to about 1 mm, from about 1 nm to about 100 nm, or any range therein. In one embodiment, the localization of plasticizer in an implant during such foam molding can be obtained by varying the amount and/or type of plasticizer in the solid polymeric materials while adding the solid polymeric materials to the foam mold as desired such that the plasticizer becomes localized in the formed implant.

In other embodiments, a stent is formed by injection molding or extrusion of a tube followed by cutting a pattern of a stent into the tube. In these embodiments, a mixture of polymer and plasticizer can be added prior to injection molding or extrusion or, in the alternative, the plasticizer can be absorbed by the stent after the stent has been formed.

In other embodiments, a polymeric coating comprising a plasticizing agent can be applied to a body of a medical article, wherein the body of the medical article can be polymeric or metal. In these embodiments, the medical article can be a stent comprising a metal body that is coated with a polymeric material to provide rigidity upon leaching of the plasticizing agent from the polymeric coating. In these embodiments, the medical article can be a stent comprising a polymeric body that is coated with a polymeric material to provide rigidity upon leaching of the plasticizing agent from the polymeric coating. It should be appreciated that any of the foregoing agents can be mixed, blended or otherwise connected with a medical device or a coating for a medical device. By way of example, a stent or a coating for a stent can contain a polymeric composition comprising paclitaxel, docetaxel, rapamycin or everolimus that can leach from the polymeric composition in vivo.

Any method of coating can be used in practicing the present invention including, but not limited to, spraying, dipping, brushing, pouring, dripping, spinning, roller coating, meniscus coating, powder coating and various inking approaches such as inkjet-type application. In some embodiments, the method of coating is spraying. In other embodiments, the method of coating is dipping. In other embodiments, additional process steps are necessary such as, for example, the application of heat or energy to medical device and/or coating.

In some embodiments, the plasticizing agent can be localized in an implant by later adding a highly-penetrating plasticizing agent to select regions of the implant. In some of these embodiments, the plasticizing agent can be any of the plasticizing agents taught above. In other of these embodiments, the plasticizing agent can also be a solvent with some ability to solubilize, and thus enter, a polymeric material in the implant. Methods of applying the plasticizing agent can include, but are not limited to, the coating methods taught herein.

The solvent may be chosen based on several criteria including, for example, its polarity, molecular size, biocompatibility, reactivity and purity. Other physical characteristics of the solvent may also be taken into account, including the solubility limit of the polymer in the solvent; oxygen and other gases in the solvent; the viscosity and vapor pressure of the combined solvent and polymer; the ability of the solvent to diffuse through an underlying material; and the thermal stability of the solvent. One of skill in the art has access to scientific literature and data regarding the solubility of a wide variety of polymers. Furthermore, one of skill in the art will appreciate that the choice of solvent may begin empirically by calculating the Gibb's free energy of dissolution using available thermodynamic data. Such calculations allow for a preliminary selection of potential solvents to test in a laboratory. It is recognized that process conditions can affect the chemical structure of the underlying materials and, thus, affect their solubility in a solvent. It is also recognized that the kinetics of dissolution are a factor to consider when selecting a solvent, because a slow dissolution of a material may not affect the performance characteristics of a product where the product is produced relatively quickly.

The solvents can include, but are not limited to, chloroform, dimethyl acetamide (DMAC), dimethyl formamide (DMF), tetrahydrofuran (THF), cyclohexanone, xylene, toluene, acetone, water, methanol, ethanol, propanol, i-propanol, methyl ethyl ketone, propylene glycol monomethyl ether, methyl butyl ketone, ethyl acetate, n-butyl acetate, dioxane and combinations thereof. Examples of solvent combinations include, but are not limited to, chloroform and acetone (50/50); DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); acetone, xylene and FLUX REMOVER AMS® (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, Inc.) (10:40:50 w/w); and 1,1,2-trichloroethane and chloroform (80:20 w/w). In some embodiments, the solvents can be polar. In these embodiments, the polar solvents can include acetone, methanol, ethanol, or i-propanol. In other embodiments, the solvents can be non-polar. In these embodiments, the solvents can include acetone, chloroform, carbon tetrachloride, tetrachloroethylene, or dichloromethane. In other embodiments, the solvents can be amphiphilic. In other embodiments, the solvents can be an alkyl halide such as, for example, methylene chloride or ethylene dichloride. In other embodiments, the solvents can be rated as Class 3 solvents according to the ICH Guidelines (Guidance for Industry, Q3C Impurities: Residual Solvents, CDER, Rockville, Md. 20857). In other embodiments, the solvents can be rated as Class 2 solvents according to the ICH Guidelines. See Id. In other embodiments, the solvents can be rated as Class 1 solvents according to the ICH Guidelines. See Id.

In some embodiments, a pore forming agent can be used to create porosity in a polymeric composition to, for example, aid in the introduction of plasticizer into a polymeric material and the leaching of plasticizer from the polymeric material. Porosity can be introduced in the polymeric compositions by any method known to one of skill in the art. In one embodiment, the porosity can be introduced into a medical article by adding particles to a polymeric material used to form the medical article and later removing the particles to create a porous structure. Pore size can be controlled by screening the particles according to size and adding particles of a predetermined size to the materials. The particles may include, but are not limited to, salts and water-soluble polymers.

In some embodiments, water-soluble polymers include, for example, polymeric salts, polyvinyl alcohol, polyethylene glycol, polyethylene oxide, glucose, dextran, dextrose, lactose, and combinations thereof. Such particles may be removed, for example, by washing in water or a very dilute acid bath. Examples of non-polymeric salts include, but are not limited to, NaCl and sodium bicarbonate. In other embodiments, the methods of forming the porous structure include stretching the polymeric material to its desired dimensions induce formation of pores or voids in the material. In other embodiments, the methods of forming the porous structure include precipitation of a cast polymer solution in an aqueous liquid such as, for example, water, prior to curing. In other embodiments, the methods of forming the porous structure include pressuring and sintering a powder of a polymer to form a structure with internal bridging that may be stretched to control the size of the pore structure created; and, bombardment of a polymeric material with high-energy particles followed by chemical etching to create a pore structure.

In some embodiments, a layer is "porous" when it has a void-to-volume percentage that ranges from about 40% to about 90%, from about 70% to about 80%, or any range therein. In some embodiments, a layer is "non-porous" when it has a void-to-volume percentage that ranges from about 0% to about 5%, from about 1% to about 3%, and any range therein. The "void-to-volume percentage" is defined as the volume of the pores divided by the total volume of the layer including the volume of the pores. In some embodiments, the void-to-volume percentage can be measured using standard test method BSR/AAMI/ISO 7198, which has been adopted in-whole as a revision of ANSI/AAMI VP20-1994 (Cardiovascular Implants—Vascular Prosthesis section 8.2.1.2, Method for Gravimetric Determination of Porosity, Am. Nat'l Stds. Inst./Assoc. for the Adv. of Med. Instr.)

In other embodiments, the implant comprises an osmotic pump to enhance leaching of the plasticizer from a medical article such as, for example, a medical implant. In these embodiments, the osmotic pump can include a polymeric material having an agent and a porous structure that can release the agent. Fluid enters the porous material and creates an osmotic pressure that induces release of the agent in vivo. In some embodiments, the osmotic pump can include an osmotic agent such as, for example, a plasticizing agent in salt form, which acts to imbibe water from the surrounding medium through the porous structure. Pressure is generated within a medical article such as, for example, a stent, and forces the plasticizing agent out of the device through the porous structure.

EXAMPLES

Example 1

The strain-to-failure of a specimen of a material can be tested using Test Procedure ASTM D882. Specimens used in the testing can be 1"×6" strips cut from a thin sheet or film for use in this procedure.

The specimens can be placed in the grips of an Instron Universal Tester and pulled until failure. For the ASTM D882 test procedure, the speed at which a specimen is stressed and the separation of the grip device on the specimen are based on the elongation to break of the material. The elongation and tensile modulus can be calculated from the displacement of the crossheads of the grip device, or with an extensometer. Since the materials of the present invention are used in an organ of a living subject, the materials should be tested at the temperature present in the subject. A thermal chamber can be installed on the Instron Universal Tester. The chamber is designed to allow the test mounts from the base and crosshead of the Instron to pass through the top and bottom of the chamber. Standard test fixtures are installed inside the chamber, and testing is conducted inside the controlled thermal environment. The chamber has internal electric heaters for elevated temperatures and uses external carbon dioxide gas as a coolant for reduced temperatures.

Example 2

A stent can be formed using standard formation techniques and a plasticizer can then be absorbed by the formed stent. The stent can be formed by first forming a poly(L-lactide) cylindrical tube that is approximately 1.0 inches in length with an outer diameter of approximately 0.053 inches and a wall-thickness of approximately 0.006 inches. The tube can be formed by injection molding. The stent pattern can be cut into the tube using an appropriate laser source.

The formed stent can then be dipped into acetone for about 15 seconds to allow the poly(L-lactide) material to absorb some acetone, which can serve as the leachable plasticizer during placement of the stent in a subject.

While particular embodiments of the present invention have been shown and described, it will be obvious to those skilled in the art that changes and modifications can be made without departing from this invention in its broader aspects. One of skill in the art will appreciate that the any of the teachings can be used together or in combination to fulfill the purpose and nature of the invention.

We claim:

1. A medical article comprising
an implant comprising a polymeric material,
wherein the polymeric material comprises a plasticizing agent capable of increasing a strain-to-failure in the polymeric material so as to prevent or reduce a formation of cracks in the polymeric material while placing the implant in a subject, wherein the plasticizing agent is localized in high-strain regions of the implant such that the high-strain regions have more of the plasticizing agent than regions outside of the high-strain regions, the high strain regions comprising regions that bend during placement of the implant,
wherein the plasticizing agent leaches from the polymeric material after placing the implant in a subject to provide rigidity in the polymeric material, and
wherein the plasticizing agent leaches from the polymeric material in less than an amount of time necessary for a required dimension of the implant to change in response to a stress in a manner that affects the clinical utility of the implant.

2. The medical article of claim 1, wherein the implant comprises an expandable component that is adapted to expand mechanically or self-expand.

3. The medical article of claim 2, wherein the expandable component is configured to expand by application of pressure from a balloon of a catheter.

4. The medical article of claim 1, wherein the implant comprises a stent or a vena cava filter.

5. The medical article of claim 4, wherein the stent is selected from a group consisting of vascular stents, renal stents, biliary stents, pulmonary stents and gastrointestinal stents.

6. The medical article of claim 1, wherein the implant comprises a biodegradable polymer.

7. The medical article of claim 1, wherein the implant comprises a polymer selected from a group consisting of polyesters, poly(ester amides); amino acids; poly(ethylene glycol) (PEG) and/or alcohol groups, polycaprolactones, poly(L-lactide), poly(D,L-lactide), poly(D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters), polyalkylene oxalates, polyphosphazenes, PHA-PEG, poly(tyrosine carbonates), poly(tyrosine arylates), polyanhydrides, poly(hydroxyethyl methacylate), poly(N-acylhydroxyproline)esters, poly(N-palmitoyl hydroxyproline)esters, polyphosphazenes, and any derivatives, analogs, homologues, congeners, salts, copolymers and combinations thereof.

8. The medical article of claim 7, wherein the PHA is selected from a group consisting of poly($\alpha$-hydroxyacids), poly($\beta$-hydroxyacids), poly(3-hydroxybutyrate), poly(3-hydroxybutyrate-co-valerate), poly(3-hydroxyproprionate), poly(3-hydroxyhexanoate), poly(4-hydroxybutyrate), poly(4-hydroxyvalerate), or poly(4-hydroxyhexanoate), poly(hydroxyvalerate), and any derivatives, analogs, homologues, congeners, salts, copolymers and combinations thereof.

9. The medical article of claim 1, wherein the plasticizing agent comprises a component that is diagnostic, bioactive, biobenefical, or a combination thereof.

10. The medical article of claim 1, wherein the plasticizing agent comprises a component that is water-soluble, lipid soluble, or a combination thereof.

11. The medical article of claim 1, wherein the plasticizing agent comprises a component that is biodegradable.

12. The medical article of claim 1, wherein the plasticizing agent comprises a component selected from a group consisting of lactic acid oligomers; dimers of cyclic lactic acid and glycolic acid; hydrogen bond forming organic compounds; polyols; alkanols; sugar alcohols and anhydrides of sugar alcohols; polyethers; esters; polyesters; aliphatic acids; saturated and unsaturated fatty acids; fatty acid esters; fatty alcohols; cholesterol; steroids; phospholipids; proteins; oils; silicones; acetylated monoglycerides; diglycerides; triglycerides; amides; acetamides; sulfoxides; sulfones; pyrrolidones; oxa acids; diglycolic acids; and any derivatives, analogs, homologues, congeners, copolymers and combinations thereof.

13. The medical article of claim 1, wherein the plasticizing agent comprises a component selected from a group consisting of lactic acid; dimers of cyclic lactic acid and glycolic acid; poly(propylene glycol), poly(vinyl pyrrolidone), phosphorylcholine, glycosaminoglycans, phospholipids, carboxymethylcellulose, hyaluronic acid, heparin, hirudin, poly(acrylamide methyl propane sulfonic acid), poly(styrene sulfonate), sulfonated dextran, dermatan sulfate, RGD, collagen, chitin, chitosan, elastin and any derivatives, analogs, homologues, congeners, salts, copolymers and combinations thereof.

14. The medical article of claim 13, wherein the poly(ethylene glycol) has a molecular weight of less than 1500 Daltons.

15. The medical article of claim 1, wherein the plasticizing agent comprises a component selected from a group consisting of castor oil, fish oil, garlic oil, ethanol, xylene, dimethyl formamide, dimethyl sulfoxide, propylene glycol, glycerol, lecithin, and derivatives and combinations thereof.

16. The medical article of claim 1, wherein the plasticizing agent leaches sufficiently from the implant in a subject in less than an amount of time required for a change in a required dimension of the implant in an amount ranging from about 0.1% to about 50%.

17. The medical article of claim 16, wherein the implant comprises a stent or a vena cava filter, the required dimension is a diameter of the stent or vena cava filter following deployment of the stent or vena cava filter in a subject, and the change is a reduction in the diameter of the stent or vena cava filter ranging from about 0.1% to about 20%.

18. The medical article of claim 1, wherein the implant comprises pores that were created through the use of a pore forming agent.

19. The medical article of claim 1, wherein the implant comprises an osmotic pump to enhance the leaching of the plasticizer from the implant.

20. The medical article of claim 1, wherein the polymeric material comprises a polymeric matrix, the plasticizing agent being mixed or dispersed within the polymeric matrix.

* * * * *